United States Patent [19]

Shimada et al.

[11] Patent Number: 5,418,231
[45] Date of Patent: May 23, 1995

[54] PYRIMIDO-BENZOTHIAZINES

[75] Inventors: Kaoru Shimada, Setagaya; Yuji Shishido, Chita, both of Japan

[73] Assignee: Pfizer Inc., New York, N.Y.

[21] Appl. No.: 78,315

[22] PCT Filed: Dec. 16, 1991

[86] PCT No.: PCT/US91/09161

§ 371 Date: Jun. 28, 1993

§ 102(e) Date: Jun. 28, 1993

[87] PCT Pub. No.: WO92/12161

PCT Pub. Date: Jul. 23, 1992

[30] Foreign Application Priority Data

Jan. 7, 1991 [JP] Japan .................. 3-000159

[51] Int. Cl.⁶ .................. C07D 513/04; A61K 31/54
[52] U.S. Cl. .................. 514/224.5; 544/34
[58] Field of Search .................. 514/224.5; 544/34

[56] References Cited

U.S. PATENT DOCUMENTS 3,483,198  12/1969  Goldman .................. 260/243
4,845,083  4/1989  Fortin et al. .................. 514/80

FOREIGN PATENT DOCUMENTS 1695595  1/1972  Germany .

OTHER PUBLICATIONS

Shimada et al., Chemical Abstracts, vol. 117, entry 234028b (1992).

M. Sako et. al., 12th Symposium on Progress in Organic Reactions and Syntheses, 1985.

M. Sako et. al., Chem. Pharm. Bull., 32(6) 2474–2476 (1984).

T. Hiramatsu et. al., J. C. S. Chem. Comm., 1977, 557–558.

*Primary Examiner*—John M. Ford
*Attorney, Agent, or Firm*—Peter C. Richardson; Gregg C. Benson; Mervin E. Brokke

[57] ABSTRACT

This invention relates to novel pyrimido-benzothiazine derivative compounds.

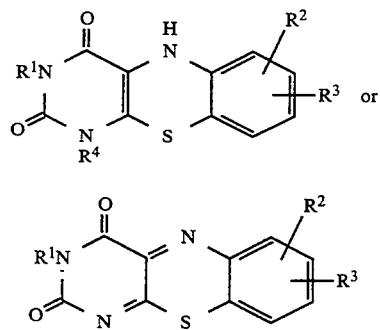

The compounds of the present invention inhibit the action of the lipoxygenase enzyme and are useful in the treatment or alleviation of inflammatory diseases, allergy and cardiovascular diseases in mammals. This invention also relates to pharmaceutical compositions comprising such compounds.

18 Claims, No Drawings

PYRIMIDO-BENZOTHIAZINES

This application is a 371 of PCT/US91/09161, filed Dec. 16, 1991.

TECHNICAL FIELD

This invention relates to novel pyrimido-benzothiazine derivative compounds. The compounds of the present invention inhibit the action of the lipoxygenase enzyme and are useful in the treatment or alleviation of inflammatory diseases, allergy and cardiovascular diseases in mammals. This invention also relates to pharmaceutical compositions comprising such compounds.

BACKGROUND ART

Arachidonic acid is known to be the biological precursor of several groups of endogenous metabolites, prostaglandins including prostacyclins, thromboxanes and leukotrienes. The first step of arachidonic acid metabolism is the release of arachidonic acid and related unsaturated fatty acids from membrane phospholipids via the action of phospholipase. Free fatty acids are then metabolized either by cyclooxygenase to produce the prostaglandins and thromboxanes or by lipoxygenase to generate hydroperoxy fatty acids which may be further converted to the leukotrienes. Leukotrienes have been implicated in the pathophysiology of inflammatory diseases including rheumatoid arthritis, gout, asthma, ischemia reperfusion injury, psoriasis and inflammatory bowel disease. Compounds that inhibit lipoxygenase are expected to provide significant new therapy for both acute and chronic inflammatory conditions.

Recently, several review articles on lipoxygenase inhibitors have been reported. See H. Masamune and L. S. Melvin, Sr., in: Annual Reports in Medicinal Chemistry 24 (1989) pp. 71–80 (Academic); and B. J. Fitzsimmons and J. Rokach in: *Leukotrienes and Lipoxygenases* (1989) pp. 427–502 (Elsevier).

Offenlegungsschrift 1695595 discloses certain pyrimido-benzothiazines which are useful for blocking phosphodiesterases. Sakamuki, M. et al. and Sako, M. et al. both in 12th Symposium on Progress in Organic Reactions and Syntheses, Symposium Papers, Nov. 8–9, 1985, Nagoya, pp. 186–189 and p. 190; and Sako, M. et al., Chem. Pharm. Bull., 32, pp. 2474–2476 (1984), disclose the syntheses of certain pyrimido-benzothiazines.

Certain derivatives of phenothiazine of the general formula

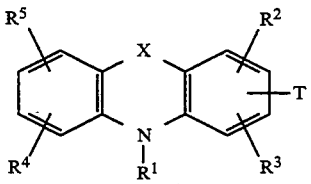

wherein X is, inter alia, S, SO or $SO_2$; $R^1$ is, inter alia, H or $(C_1-C_6)$alkyl; $R^2$, $R^3$, $R^4$ and $R^5$ are inter alia, independently H, $(C_1-C_6)$alkyl, $(C_2-C_6)$alkenyl or $-(CH_2)_n M$ where n is 0–6 and M is halogen or various groups and T is H or $OR^{15}$ where $R^{15}$ is H or various groups are disclosed in EP 138481, published Apr. 24, 1985 and corresponding to JP 60155165, as leukotriene biosynthesis inhibitors useful in treating allergic conditions, asthma, cardiovascular disorders, inflammation and certain skin diseases.

DISCLOSURE OF THE INVENTION

The present invention provides pyrimido-benzothiazine derivative compounds of the following formulae:

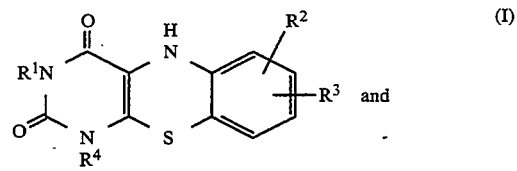

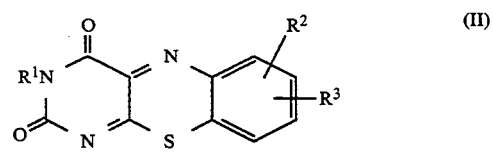

and the pharmaceutically-acceptable salts thereof, wherein $R^1$ is hydrogen or $(C_1-C_6)$alkyl; $R^2$ is hydrogen, halogen, $(C_1-C_6)$alkyl, $(C_1-C_6)$alkoxy or $(C_1-C_6)$halosubstituted alkyl; $R^3$ is hydrogen or $(C_1-C_6)$alkyl; $R^4$ is hydrogen, $(C_1-C_6)$alkyl, $(C_3-C_8)$cycloalkyl, $(C_1-C_6)$alkoxy-$(C_1-C_6)$alkyl or aryl-$(C_1-C_6)$alkyl; provided that in formula (I), $R^1$, $R^2$, $R^3$ and $R^4$ are not simultaneously hydrogen, $R^2$, $R^3$ and $R^4$ are not simultaneously hydrogen when $R^1$ and $R^4$ are respectively methyl; provided further that in formula (II), $R^1$, $R^2$ and $R^3$ are not simultaneously hydrogen and $R^2$ and $R^3$ are not simultaneously hydrogen when $R^1$ is methyl; and provided further still that the groups $R^2$ and $R^3$ may be attached to any available position on the ring in formula (I) or (II).

A preferred group of compounds comprises compounds of formula (I) wherein $R^1$ is $(C_1-C_6)$alkyl. Also preferred are compounds of formula (I) wherein $R^1$ is methyl and $R^2$ is halogen, $(C_1-C_6)$alkyl or $(C_1-C_6)$alkoxy. Another preferred group of compounds comprises compounds of formula (II) wherein $R^1$ is $(C_1-C_6)$alkyl. Also preferred are compounds of formula (II) wherein $R^1$ is methyl and $R^2$ is halogen, $(C_1-C_6)$alkyl, $(C_1-C_6)$alkoxy or $(C_1-C_6)$halosubstituted alkyl.

In formulae (I) and (II), above, and throughout this specification and the appendant claims, the term "halogen" is used to mean radicals derived from the elements fluorine, chlorine, bromine and iodine;

the term "alkyl" is used to mean straight or branched chain radicals, including, but not limited to, methyl, ethyl, n-propyl, isopropyl, butyl and the like;

the term "alkoxy" is used to mean $-OR_5$ wherein $R_5$ is an alkyl radical, including, but not limited to, methoxy, ethoxy, propoxy, isopropoxy, butoxy and the like;

the term "halosubstituted alkyl" refers to an alkyl radical as described above substituted with one or more halogens, including, but not limited to chloromethyl, trifluoromethyl, 2,2,2-trichloroethyl and the like;

the term "alkoxyalkyl" is used to mean $-R_6 OR_7$ wherein $R_6$ and $R_7$ are respectively alkyl radicals, including, but not limited to methoxymethyl, methoxyethyl, ethoxymethyl, ethoxyethyl and the like;

the term "arylalkyl" means an aryl group appended to an alkyl radical including, but not limited to, phenylmethyl(benzyl), phenylethyl, 2-phenylethyl, phenylpropyl and 2-pyridylmethyl, and the like;

the term "cycloalkyl" is used to mean carbocyclic radicals, including, but not limited to, cyclopropyl, cyclobutyl, cyclopentyl, cyclohexyl, and the like.

Certain of the compounds of the above formula may form acid salts. The pharmaceutically-acceptable acid salts are those formed from acids which yield non-toxic acid salts, for example, hydrochloride, hydrobromide, sulfate or bisulfate, phosphate or acid phosphate, acetate, citrate, fumarate, gluconate, lactate, maleate, succinate, tartrate, methanesulfonate, benzenesulfonate, toluenesulfonate, and formate salts.

This invention includes pharmaceutical compositions for treatment of inflammatory diseases, allergy and cardiovascular diseases in a mammal which comprises a pharmaceutically-acceptable carrier or diluent and a compound of the above formula (I) or (II) or a pharmaceutically-acceptable salt thereof.

This invention further includes methods for treating inflammatory diseases, allergy and cardiovascular diseases in a mammal which comprise administering to said mammal an effective amount of a compound of the above formula (I) or (II) or a pharmaceutically-acceptable salt thereof.

DETAILED DESCRIPTION

The compounds of formulae (I) and (II), above, can be prepared by any of a number of synthetic methods. A preferred method is shown in Scheme A and described below wherein $R^1$, $R^2$, $R^3$ and $R^4$ are as described above.

II, D. J. Brown, An Interscience Publication, John Willy & Sons, New York, 1985, Table LVIII, page 728. To the resulting pale yellow solution or suspension is added carefully an ice cold saturated aqueous $NaHCO_3$ solution. The resulting reaction mixture is refluxed, the solvent is removed and the residue is recrystallized from an appropriate solvent or chromatographed over silica-gel to give a 5-hydroxyprimidine-2,4(1H,3H)-dione derivative of formula (IV).

Then, to a solution or suspension of a 5-hydroxypyrimidine-2,4(1H,3H)-dione derivative of formula (IV) in a reaction inert solvent is added N-bromosuccinimide portion-wise at room temperature. A preferred solvent is ethanol. The reaction mixture is stirred until the derivative of formula (IV) disappears. Then, a 2-aminobenzenethiol derivative of formula (V) is added and the mixture is heated at reflux. Certain 2-aminobenzenethiol derivatives of formula (V) are commercially available and, further, the derivatives of formula (V) can be prepared from the corresponding 2-aminobenzothiazoles by hydrolysis as described by Mital, R. L., et al., J. Chem. Soc. (c), 2148 (1969). When a precipitate results after reflux of the reaction mixture, the precipitate is collected to give a 1,5-dihydro-2H-pyrimido[4,5-b][1,4]benzothiazine-2,4(3H)-dione derivative of formula (I). When no precipitate is obtained after reflux, the derivative of formula (I) is obtained by chromatographic separation on silica gel. The foregoing method for reacting derivatives of formula (IV) with derivatives of formula (V) to yield derivatives of formula (I) is analogous to the method described by Sako, M., et al., Chem. Pharm. Bull., 32, 2474 (1984).

When derivative compounds of formula (II) are desired, a solution or suspension of 1,5-dihydro-2H-

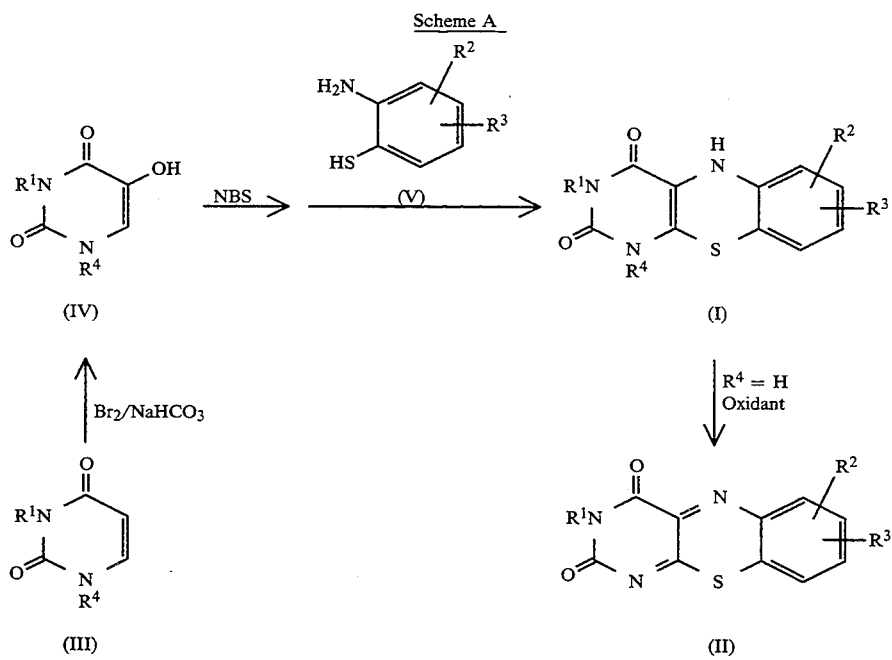

According to the synthetic method shown in Scheme A, above, bromine is added dropwise to an ice-cooled solution or suspension of a pyrimidine-2,4(1H,3H)-dione derivative of formula (III) in water until the solution or suspension is colored pale yellow. The pyrimidine-2,4(1H,3H)-dione derivatives of formula (III) are prepared, for example, by the methods described in *Heterocyclic Compounds 16, The pyrimidine supplement* pyrimido[4,5-b][1,4]benzothiazine-2,4(3H)-dione derivative of formula (I) wherein $R^4$ is hydrogen in acetonitrile is prepared. To that solution or suspension at room temperature is added, dropwise, an oxidant such as diethylazodicarboxylate, 1,4-benzoquinone or 2,3-dichloro-5,6-dicyano-1,4-benzoquinone. Alternatively, oxygen can be used as the oxidant. A preferred oxidant is diethylazodicarboxylate. The reaction mixture is stirred. When a precipitate results, the precipitate is collected an washed with diethylether to give a 2H-pyrimido[4,5-b][1,4]benzothiazine-2,4(3H)-dione derivative of formula (II). When no precipitate is obtained after oxidation, the solvent is removed from the reaction mixture, and the residue is triturated with diethylether and filtered to give a compound of formula (II).

The pharmaceutically-acceptable salts of the compounds of the present invention are readily prepared by contacting said compounds with a stoichiometric amount of, in the case of non-toxic cation, an appropriate metal hydroxide or alkoxide or amine in either aqueous solution or a suitable organic solvent; or, in the case of an non-toxic acid salt, an appropriate mineral or organic acid in either aqueous solution or a suitable organic solvent. The respective salt may then be obtained by precipitation or by evaporation of the solvent.

The compounds of this invention inhibit the activity of the lipoxygenase enzyme. This inhibition has been demonstrated by an assay using rat peritoneal cavity resident cells which determines the effect of said compounds on the metabolism of arachidonic acid as described in Jap. J Inflammation 7:145–150, 1987, "Synthesis of leukotrienes by peritoneal macrophages".

The ability of the compounds of the present invention to inhibit the lipoxygenase enzyme make them useful for controlling the symptoms induced by the endogenous metabolites arising from arachidonic acid in a mammalian subject. The compounds therefore are valuable in the prevention and treatment of disease state in which the accumulation of arachidonic acid metabolites are the causative factor, e.g., allergic bronchial asthma, skin disorders, rheumatoid arthritis, osteoarthritis and thrombosis.

Thus, the compounds of formula (I) and (II), and their pharmaceutically-acceptable salts are of particular use in the treatment or alleviation of inflammatory diseases, allergy and cardiovascular diseases in a human subject as well as in the inhibition of the lipoxygenase enzyme.

For treatment of the various conditions described above, the compounds of this invention and their pharmaceutically-acceptable salts can be administered to a human subject either alone, or preferably, in combination with practice. A compound of this invention can be administered by a variety of conventional routes of administration including oral and parenteral administration and by inhalation. When the compounds are administered orally, the dose range will be from about 0.1 to 20 mg/kg body weight of the subject to be treated per day, preferably from about 0.1 to 1.0 mg/kg per day in single or divided doses. If parenteral administration is desired, then an effective dose will be from 0.1 to 1.0 mg/kg body weight of the subject to be treated per day. In some instances it may be necessary to use dosages outside these limits, since the dosage will necessarily vary according to the age, weight and response of the individual patient as well as the severity of the patient's symptoms and the potency of the particular compound being administered.

For oral administration, the compounds of the invention and their pharmaceutically-acceptable salts can be administered, for example, in the form of tablets, powders, lozenges, syrups or capsules, or as an aqueous solution or suspension. In the case of tablets for oral use, carriers which are commonly used include lactose and corn starch. Further, lubricating agents such as magnesium stearate, are commonly added. In the case of capsules, useful diluents are lactose and dried corn starch. When aqueous suspensions are required for oral use, the active ingredient is combined with emulsifying and suspending agents. If desired, certain sweetening and/or flavoring agents can be added. For intramuscular, intraperitoneal, subcutaneous and intravenous use, a sterile solution of the active ingredient is prepared, and the pH of the solutions should be suitably adjusted and buffered. For intravenous use, the total concentration of solutes should be controlled to make the preparation isotonic.

The present invention is illustrated by the following examples. However, it should be understood that the invention is not limited to the specific details of these examples. Proton nuclear magnetic resonance spectra (NMR) were measured at 270 MHz unless otherwise indicated and peak positions are expressed in parts per million (ppm) downfield from tetramethylsilane. The peak shapes are denoted as follows: s, singlet; d, doublet; t, triplet; q, quartet; m, multiplet; br, broad.

EXAMPLE 1

3-Propyl-2H-pyrimido[4,5-b][1,4]benzothiazine-2,4(3H)-dione

A. 5-Hydroxy-3-propylpyrimidine-2,4(1H,3H)-dione

To an ice-cooled solution of 3-propylpyrimidine-2,4(1H,3H)-dione (3.00 g) in $H_2O$ (100 ml) was added dropwise bromine (1.56 g) until the solution was colored pale yellow. An ice cold saturated $NaHCO_3$ solution was added carefully to the reaction mixture. The alkalized solution was refluxed for 12 hours. After removal of the solvent, the residue was recrystallized from ethanol to give 5-hydroxy-3-propylpyrimidine-2,4(1H,3H)-dione (2.32 g, 70% yield).

B. 1,5-Dihydro-3-propyl-2H-pyrimido[4,5-b][1,4]benzothiazine-2,4(3H)-dione

To a solution of the 5-hydroxy-3-propylpyrimidine-2,4(1H,3H)-dione (0.85 g) in ethanol (40 ml), N-bromosuccinimide (0.98 g) was added in portions at room temperature. The mixture was stirred for 30 min. 2-Aminobenzenethiol (0.94 g) was added and the mixture was heated at reflux for one hour. After cooling, the precipitate was collected to give 1,5-dihydro-3-propyl-2H-pyrimido[4,5-b][1,4]benzothiazine-2,4(3H)-dione (1.20 g, 87% yield).

C. 3-Propyl-2H-pyrimido[4,5-b][1,4]benzothiazine-2,4(3H)-dione

To a solution of the 1,5-dihydro-3-propyl-2H-pyrimido[4,5-b][1,4]benzothiazine-2,4(3H)-dione (0.55 g) in acetonitrile (40 ml) was added dropwise diethylazodicarboxylate (0.52 g) at room temperature. The mixture was stirred for two hours. After the solvent was removed, the residue was triturated with diethylether and filtered to give 3-propyl-2H-pyrimido[4,5-b][1,4]benzothiazine-2,4(3H)-dione (0.43 g, 78% yield).

m.p.: 258° C. IR: (KBR)$cm^{-1}$: 2950, 1650, 1520, 1430 NMR: (DMSO-$d_6$) δ: 8.16 (1H, dd, 1.5 Hz, 8 Hz), 8.00 (1H, dd, 1.5 Hz, 8 Hz), 7.82 (1H, dt, 1.5 Hz, 8 Hz), 7.76 (1H, dt, 1.5 Hz, 8 Hz), 3.81 (2H, t, 7.5 Hz), 1.58 (2H, dt, 7.3 Hz, 7.5 Hz), 0.90 (3H, t, 7.5 Hz).

EXAMPLE 2

6-Chloro-1,5-dihydro-3-methyl-2H-pyrimido-[4,5-b][1,4]benzothiazine-2,4(3H)-dione Employing the procedure of Example 1, parts A and B with 3-methylpyrimidine-2,4(1H,3H)-dione and 2-amino-3-chlorobenzenethiol yielded the title compound.

m.p.: 268°–270° C. (dec.) IR: (KBr)cm$^{-1}$: 3360, 1697, 1638, 1463, 1307, 750 NMR: (DMSO-d$_6$) δ: 3.15 (3H,s), 6.34 (1H,s), 6.85 (1H, dd, 7.7 Hz, 8.1 Hz), 7.08 (1H, d, 7.7 Hz), 7.26 (1H, d, 8.1 Hz), 11.61(1H,s).

EXAMPLE 3

1,5-Dihydro-3,8-dimethyl-2H-pyrimido[4,5-b][1,4]benzothiazine-2,4(3H)-dione

Employing the procedure of Example 1, parts A and B with 3-methylpyrimidine-2,4(1H, 3H)-dione and 2-amino-5-methylbenzenthiol yielded the title compound.

m.p.: 285° C. (dec.) IR: (KBr)cm$^{-1}$: 3320, 2990, 1700, 1620, 1600, 1500, 1310, 815 NMR: (DMSO-d$_6$) δ: 11.30 (1H, s), 7.40 (1H, s), 6.90 (1H, d, 8 Hz) 6.78 (1H, d, 8 Hz), 3.14 (3H, s), 2.11 (3H, s).

EXAMPLE 4

1,5-Dihydro-8-methoxy-3-methyl-2H-pyrimido[4,5-b][1,4]benzothiazine-2,4(3H)-dione Employing the procedure of Example 1, parts A and B, with 3-methylpyrimidine-2,4(1H,3H)-dione and 2-amino-5-methoxybenzenethiol yielded the title compound.

m.p.: 261.4° C. IR: (KBR)cm$^{-1}$: 3325, 1700, 1617, 1498, 1305, 1227, 1034, 818, 750 NMR: (DMSO-d$_6$) δ: 3.14 (3H, s), 3.64 (3H, s), 6.60–7.50 (4H, m), 11.31 (1H, s).

EXAMPLE 5

8-Ethoxy-1,5-dihydro-3-methyl-2H-pyrimido[4,5-b][1,4]benzothiazine-2,4(3H)-dione Employing the procedure of Example 1, parts A and B, with 3-methylpyrimidine-2,4(1H,3H)-dione and 2-amino-5-ethoxybenzenethiol yielded the title compound.

m.p.: 261° C. IR: (KBR) δ: 3300, 3200, 1715, 1600, 1495, 1470 NMR: (DMSO-d$_6$) δ: 11.30 (1H, s), 7.29 (1H, s), 6.96 (1H, m) 6.60 (1H, m) 3.89 (2H, q, 7 Hz), 3.14 (3H, s), 1.25 (3H, t, 7 Hz)

EXAMPLE 6

8-Fluoro-1,5-dihydro-3-methyl-2H-pyrimido[4,5-b][1,4benzothiazine-2,4(3H)-dione

Employing the procedure of Example 1, parts A and B with 3-methylpyrimidine-2,4(1H,3H)-dione and 2-amino-5-fluorobenzenethiol yielded the title compound.

m.p.: 280° C. (dec.) IR: (KBr)cm$^{-1}$: 3280, 3080, 1717, 1694, 1604, 1496, 1472, 1307, 1250, 1198, 897, 743 NMR (DMSO-d$_6$) δ: 31.4 (3H, s), 6.86 (1H, td, 8.6, 2.6 Hz), 6.97 (1H, dd, 8.6, 2.6 Hz), 7.03 (1H, dd, 8.6, 5.1 Hz), 7.60 (1H, s), 11.37 (1H, s).

EXAMPLE 7

7-Trifluoromethyl-3-methyl-2H-pyrimido[4,5-b][1,4]benzothiazine-2,4(3H)-dione

Employing the procedure of Example 1, parts A, B and C, with 3-methylpyrimidine-2,4(1H,3H)-dione and 2-amino-4-trifluoromethylbenzenethiol yielded the title compound.

m.p.: 238° C. IR: (KBr)cm$^{-1}$: 1730, 1670, 1585, 1555, 1535, 1340, 1310, 1290, 1210, 1175, 1120, 945 NMR: (DMSO-d$_6$) δ: 8.48 (1H, s), 8.25 (1H, m), 8.16 (1H, m), 3.27 (3H, s).

EXAMPLE 8

3,8-Dimethyl-2H-pyrimido[4,5-b][1,4]benzothiazine-2,4(3H)-dione

Employing the procedure of Example 1, parts A, B and C, with 3-methylpyrimidine-2,4(1H,3H)-dione and 2-amino-5-methoxybenzenethiol yielded the title compound.

m.p.: 250° C. (dec.) IR: (KBr)cm$^{-1}$: 1700, 1665, 1515, 1440, 1115 NMR: (DMSO-d$_6$) δ: 8.07 (1H, d, 8 Hz), 7.83 (1H, s), 7.59 (1H, d, 8 Hz), 3.25 (3H, s), 2.07 (3H, s).

EXAMPLE 9

8-Ethoxy-3-2H-pyrimido[4,5-b][1,4]benzothiazine-2,4(3H)-dione

Employing the procedure of Example 1, parts A, B, and C, with 3-methylpyrimidine-2,4(1H,3H)-dione and 2-amino-5-ethoxybenzenethiol yielded the title compound.

m.p.: 280° C. (dec.) IR: (KBr)cm$^{-1}$: 1700, 1660, 1520, 1235 NMR: (DMSO-d$_6$) δ: 8.11 (1H, d, 8 Hz), 7.65 (1H, s), 7.34 (1H, d, 8 Hz), 4.26 (2H, q, 7 Hz), 3.24 (3H, s), 1.40 (3H, t, 7 Hz).

EXAMPLE 10

8-Chloro-1,5-dihydro-3-methyl-2H-pyrimido-[4,5-b][1,4]benzothiazine-2,4(3H)-dione Employing the procedure of Example 1, parts A and B, with 3-methylpyrimidine-2,4(1H,3H)-dione and 2-amino-5-chlorobenzenethiol yielded the title compound.

m.p.: 288.3° C. IR:(KBr)cm$^{-1}$: 3275, 3200, 3104, 1718, 1694, 1600, 1471, 1305, 813, 742 NMR: (DMSO-d$_6$) δ: 3.13 (3H, s), 6.97–7.05 (2H, m), 7.08 (1H, d, 2.2 Hz), 7.77 (1H, s), 11.38 (1H, s).

EXAMPLE 11

1,5-Dihydro-3,7,8-trimethyl-2H-pyrimido[4,5-b]-[1,4]benzothiazine-2,4(3H)-dione

Employing the procedure of Example 1, parts A and B, with 3-methylpyrimidine-2,4(1H,3H)-dione and 2-amino-4,5-dimethylbenzenethiol yielded the title compound.

m.p.: >300° C. IR:(KBr)cm$^{-1}$: 3340, 1698, 1621, 1300, 903, 753 NMR: (DMSO-d$_6$) δ: 2.04 (6H, s), 3.13 (3H, s), 6.71 (1H, s), 6.81 (1H, s), 7.26 (1H, s), 11.29 (1H, s).

EXAMPLE 12

1,5-Dihydro-1-methoxyethyl-3-methyl-2H-pyrimido-[4,5-b][1,4]benzothiazine-2,4(3H)-dione Employing the procedure of Example 1, parts A and B, with 1-methoxyethyl-3-methylpyrimidine-2,4(1H,3H)-dione and 2-aminobenzenethiol yielded the title compound.

m.p.: 130° C. IR:(KBr)cm$^{-1}$: 3330, 1685, 1620, 1585, 1445, 1120, 750 NMR: (DMSO-d$_6$) δ: 7.81 (1H, s), 7.03–7.14 (3H, m), 6.82 (1H, dt, 1.5 Hz, 7.3 Hz), 4.05

(2H, t, 5.5 Hz), 3.54 (2H, t, 5.5 Hz), 3.27 (3H, s), 3.21 (3H, s).

EXAMPLE 13

1,5-Dihydro-3-propyl-2H-pyrimido[4,5-b]-[1,4]benzothiazine-2,4(3H)-dione

Employing the procedure of Example 1, parts A and B, with 3-n-propylpyrimidine-2,4(1H,3H)-dione and 2-aminobenzenethiol yielded the title compound.

m.p.: 287° C. IR:(KBr)cm$^{-1}$: 3255, 1695, 1605, 1575, 1305, 1260, 930 NMR: (CDCl$_3$) δ: 11.33 (1H, s), 7.54 (1H, s), 6.93–7.00 (3H, m), 6.76 (1H, m), 3.73 (2H, t, 7.3 Hz), 1.53 (2H, m), 0.84 (3H, t, 7.3 Hz).

EXAMPLE 14

3-Butyl-1,5-dihydro-2H-pyrimido[4,5-b]-[1,4]benzothiazine-2,4(3H)-dione

Employing the procedure of Example 1, parts A and B, with 3-butylpyrimidine-2,4(1H,3H)-dione and 2-aminobenzenethiol yielded the title compound.

m.p.: 277°–278° C. (dec.) IR:(KBr)cm$^{-1}$: 3300, 3100, 2960, 1712, 1603, 1465, 1306, 1260, 753, 740 NMR: (DMSO-d$_6$) δ: 0.89 (3H, t, 7.3 Hz), 1.27 (2H, qt, 7.3, 7.2 Hz), 1.50 (2H, tt, 7.3, 7.2 Hz), 3.77 (2H, t, 7.3 Hz), 6.72–6.77 (1H, m), 6.94 (1H, d, 7.3 Hz), 6.97–7.00 (2H, m), 7.54 (1H, s), 11.33 (1H, s).

EXAMPLE 15

1,5-Dihydro-1-isopropyl-3-methyl-2H-pyrimido-[4,5-b][1,4]benzothiazine-2,4(3H)-dione Employing the procedure of Example 1, parts A and B, with 1-isopropyl-3-methylpyrimidine-2,4(1H,3H)-dione and 2-aminobenzenethiol yielded the title compound.

m.p.: 167° C. IR:(KBr)cm$^{-1}$: 3330, 3280, 1690, 1630, 1455, 745 NMR: (CDCl$_3$) δ: 7.09 (1H, dt, 1.5 Hz, 8 Hz), 7.01 (1H, d, 8 Hz), 6.87 (1H, dt, 1.5 Hz, 8 Hz), 6.72 (1H, dd, 1.5 Hz, 8 Hz), 6.26 (1H, s), 4.85 (1H, sev, 7 Hz), 3.34 (3H, s), 1.58 (6H, d, 7 Hz).

EXAMPLE 16

7-Trifluoromethyl-1,5-dihydro-3-methyl-2H-pyrimido-[4,5-b][1,4]benzothiazine-2,4(3H)-dione Employing the procedure of Example 1, parts A and B, with 3-methylpyrimidine-2,4(1H,3H)-dione and 2-amino-4-trifluoromethylbenzenethiol yielded the title compound.

m.p.: >300° C. IR:(KBr)cm$^{-1}$: 3350, 1710, 1610, 1330, 1120, 940, 750 NMR: (DMSO-d$_6$) δ: 11.45 (1H, s), 7.97 (1H, d, 1.8 Hz), 7.14 (1H, d, 8 Hz), 7.01 (1H, dd, 8 Hz, 1.8 Hz).

EXAMPLE 17

7-Trifluoromethyl-1,5-dihydro-3-propyl-2H-pyrimido[4,5-b][1,4]benzothiazine-2,4(3H)-dione . Hydrobromide Employing the procedure of Example 1, parts A and B, with 3-n-propylpyrimidine-2,4(1H,3H)-dione and 2-amino-4-trifluoromethylbenzenethiol yielded the title compound.

m.p.: >300° C. IR:(KBr)cm$^{-1}$: 3280, 1710, 1610, 1460, 1330, 1120 NMR: (DMSO-d$_6$) δ: 11.43 (1H, s), 7.96 (1H, s), 7.34 (1H, s), 7.17 (1H, d, 8 Hz), 7.03 (1H, d, 8 Hz), 3.73 (2H, t, 7.3 Hz), 1.53 (2H, m), 0.85 (3H, t, 7.3 Hz).

EXAMPLE 18

3-Butyl-7-trifluoromethyl-1,5-dihydro-2H-pyrimido-[4,5-b][1,4]benzothiazine-2,4(3H)-dione Employing the procedure of Example 1, parts A and B, with 3-butylpyrimidine-2,4(1H,3H)-dione and 2-amino-4-trifluoromethylbenzenethiol yielded the title compound.

m.p.: >300° C. IR:(KBr)cm$^{-1}$: 3250, 2975, 1710, 1610, 1460, 1330, 950, 750 NMR: (DMSO-d$_6$) δ: 0.89 (2H, t, 7.3 Hz), 1.27 (2H, qt, 7.3, 7.3 Hz), 1.50 (2H, tt, 7.3, 7.1 Hz), 3.76 (2H, t, 7.1 Hz), 7.02 (1H, dd, 8.1, 1.5 Hz), 7.15 (1H, d, 8.1 Hz), 7.34 (1H, d, 1.5 Hz), 7.95 (1H, s), 11.4 (1H, s).

EXAMPLE 19

1-Cyclopentyl-1,5-dihydro-3-methyl-2H-pyrimido-[4,5-b][1,4]benzothiazine-2,4(3H)-dione Employing the procedure of Example 1, parts A and B, with 1-cyclopentyl-3-methylpyrimidine-2,4(1H,3H)-dione and 2-aminobenzenethiol yielded the title compound.

m.p.: 166° C. IR:(KBr)cm$^{-1}$: 3400, 1690, 1630, 1480, 1340, 1300, 1180 NMR: (CDCl$_3$) δ: 7.08 (1H, dt, 1.5 Hz, 7.5 Hz), 7.01 (1H, dd, 1.5 Hz, 7.5 Hz), 6.87 (1H, dt, 1.5 Hz, 7.5 Hz), 6.71 (1H, dd, 1.5 Hz, 7.5 Hz), 6.25 (1H, s), 4.75 (1H, s), 3.35 (3H, s), 2.21 (2H, m), 1.95 (4H, m), 1.60 (2H, m).

EXAMPLE 20

1-Benzyl-1,5-dihydro-3-methyl-2H-pyrimido[4,5-b]-[1,4]benzothiazine-2,4(3H)-dione Employing the procedure of Example 1, parts A and B, with 1-benzyl-3-methylpyrimidine-2,4(1H,3H)-dione and 2-aminobenzenethiol yielded the title compound.

m.p.: 193° C. IR:(KBr)cm$^{-1}$: 3320, 1685, 1625, 1580, 1460, 740 NMR: (DMSO-d$_6$) δ: 7.88 (1H, s), 7.28–7.37 (5H, m), 7.08 (1H, m), 7.06 (1H, m), 6.94 (1H, m), 6.81 (1H, m), 5.14 (2H, s), 3.25 (3H, s).

EXAMPLE 21

6-Chloro-3-methyl-2H-pyrimido[4,5-b]-[1,4]benzothiazine-2,4(3H)-dione

Employing the procedure of Example 1, parts A, B and C, with 3-methylpyrimidine-2,4(1H,3H)-dione and 2-amino-3-chlorobenzenethiol yielded the title compound.

m.p.: 271°–273° C. (dec.) IR:(KBr)cm$^{-1}$: 1716, 1662, 1527, 1130, 787, 742 NMR: (DMSO-d$_6$) δ: 3.16 (3H, s), 7.60–7.78 (3H, m).

EXAMPLE 22

8-Fluoro-3-methyl-2H-pyrimido[4,5-b]-[1,4]benzothiazine-2,4(3H)-dione

Employing the procedure of Example 1, parts A, B and C, with 3-methylpyrimidine-2,4(1H,3H)-dione and 2-amino-5-fluorobenzenethiol yielded the title compound.

m.p.: >300° C. IR:(KBr)cm$^{-1}$: 1571, 1518, 1293, 1278, 1230, 1216, 1138, 1118 NMR: (DMSO-d$_6$) δ: 3.25 (3H, s), 7.63 (1H, td, 8.8, 2.9 Hz), 8.05 (1H, dd, 8.8, 2.9 Hz), 8.26 (1H, dd, 5.7, 8.8 Hz).

EXAMPLE 23

8-Methoxy-3-methyl-2H-pyrimido[4,5-b]-[1,4]benzothiazine-2,4(3H)-dione

Employing the procedure of Example 1, parts A, B and C, with 3-methylpyrimidine-2,4(1H,3H)-dione and 2-amino-5-methoxybenzenethiol yielded the title compound.

m.p.: 258.5° C. IR:(KBr)cm$^{-1}$: 1700, 1654, 1511, 1339, 1233, 1118 NMR: (DMSO-d$_6$) δ: 3.24 (3H, s), 3.97 (3H, s), 7.35 (1H, dd, 8.8, 2.9 Hz), 7.67 (1H, d, 2.9 Hz), 8.11 (1H, d, 8.8 Hz).

EXAMPLE 24

3,7,8-Trimethyl-2H-pyrimido[4,5-b]-[1,4]benzothiazine-2,4(3H)-dione

Employing the procedure of Example 1, parts A, B and C, with 3-methylpyrimidine-2,4(1H,3H)-dione and 2-amino-4,5-dimethylbenzenethiol yielded the title compound.

m.p.: >300° C. IR:(KBr)cm$^{-1}$: 1703, 1680, 1522, 1237, 1128 NMR: (DMSO-d$_6$) δ: 2.40 (3H, s), 2.42 (3H, s), 3.25 (3H, s), 7.81 (1H, s), 8.01 (1H, s).

EXAMPLE 25

3-Butyl-2H-pyrimido[4,5-b][1,4]benzothiazine-2,4(3H)-dione

Employing the procedure of Example 1, parts A, B and C, with 3-butylpyrimidine-2,4(1H,3H)-dione and 2-aminobenzenethiol yielded the title compound.

m.p.: 250°-251° C. IR:(KBr)cm$^{-1}$: 1717, 1650, 1518, 1428, 780

We claim:

1. A compound of formula

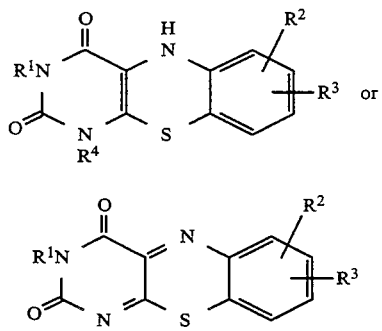

and the pharmaceutically-acceptable salts thereof, wherein R$^1$ is hydrogen or (C$_1$-C$_6$)alkyl; R$^2$ is hydrogen, halogen, (C$_1$-C$_6$)alkyl, (C$_1$-C$_6$)alkoxy or (C$_1$-C$_6$)halosubstituted alkyl; R$^3$ is hydrogen or (C$_1$-C$_6$)alkyl; R$^4$ is hydrogen, (C$_1$-C$_6$)alkyl, (C$_3$-C$_8$)cycloalkyl, (C$_1$-C$_6$)alkoxy-(C$_1$-C$_6$)alkylphenyl-(C$_1$-C$_6$)alkyl or pyridyl-(C$_1$-C$_6$)alkyl; provided that in formula (I), R$^1$, R$^2$, R$^3$ and R$^4$ are not simultaneously hydrogen, R$^2$, R$^3$ and R$^4$ are not simultaneously hydrogen when R$^1$ is methyl and R$^2$ and R$^3$ are not simultaneously hydrogen when R$^1$ and R$^4$ are respectively methyl; provided further that in formula (II), R$^1$, R$^2$ and R$^3$ are not simultaneously hydrogen and R$^2$ and R$^3$ are not simultaneously hydrogen when R$^1$ is methyl; and provided further still that the groups R$^2$ and R$^3$ may be attached to any available position on the ring in formula (I) or (II).

2. A compound according to claim 1 of the formula

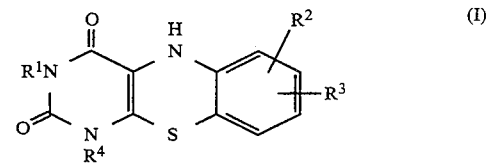

or a pharmaceutically-acceptable salt thereof wherein R$^1$, R$^2$, R$^3$ and R$^4$ are as defined in claim 1.

3. A compound according to claim 1 of the formula

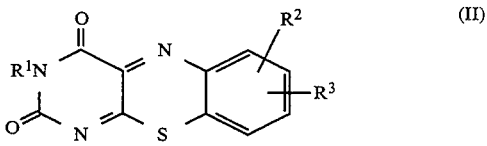

or a pharmaceutically-acceptable salt thereof wherein R$^1$, R$^2$, R$^3$ and R$^4$ are as defined in claim 1.

4. A compound or a pharmaceutically-acceptable salt thereof according to claim 2 wherein R$^1$ is (C$_1$-C$_6$)alkyl.

5. A compound or a pharmaceutically-acceptable salt thereof according to claim 4 wherein R$^1$ is methyl.

6. A compound or a pharmaceutically-acceptable salt thereof according to claim 5 wherein R$^2$ is halogen.

7. A compound or a pharmaceutically-acceptable salt thereof according to claim 5 wherein R$^2$ is (C$_1$-C$_6$)alkyl.

8. A compound or a pharmaceutically-acceptable salt thereof according to claim 5 wherein R$^2$ is (C$_1$-C$_6$)alkoxy.

9. A compound or a pharmaceutically-acceptable salt thereof according to claim 3 wherein R$^1$ is (C$_1$-C$_6$)alkyl.

10. A compound or a pharmaceutically-acceptable salt thereof according to claim 9 wherein R$^1$ is methyl.

11. A compound or a pharmaceutically-acceptable salt thereof according to claim 10 wherein R$^2$ is halogen.

12. A compound or a pharmaceutically-acceptable salt thereof according to claim 10 wherein R$^2$ is (C$_1$-C$_6$)alkyl.

13. A compound or a pharmaceutically-acceptable salt thereof according to claim 10 wherein R$^2$ is (C$_1$-C$_6$)alkoxy.

14. A compound or a pharmaceutically-acceptable salt thereof according to claim 10 wherein R$^2$ is (C$_1$-C$_6$)halo-substituted alkyl.

15. A pharmaceutical composition for the treatment of an allergic condition, inflammatory condition or cardiovascular disease in a mammal which comprises an effective amount of a compound according to claim 1 or a pharmaceutically-acceptable salt thereof and a pharmaceutically-acceptable diluent or carrier.

16. A method for treating an allergic condition in a mammal which comprises administering to said mammal an effective amount of a compound according to claim 1 or a pharmaceutically-acceptable salt thereof.

17. A method for treating an inflammatory condition in a mammal which comprises administering to said mammal an effective amount of a compound according to claim 1 or a pharmaceutically-acceptable salts thereof.

18. A method for treating a cardiovascular disease in a mammal which comprises administering to said mammal an effective amount of a compound according to claim 1 or a pharmaceutically-acceptable salt thereof.

* * * * *